United States Patent
Lampalzer

(10) Patent No.: US 9,204,952 B2
(45) Date of Patent: Dec. 8, 2015

(54) METHOD FOR OPTICAL 3D MEASUREMENT OF TEETH WITH REDUCED POINT SPREAD FUNCTION

(71) Applicant: smart optics Sensortechnik GmbH, Bochum (DE)

(72) Inventor: Ralf Lampalzer, Witten (DE)

(73) Assignee: Smart Optics Sensortechnik GmbH, Bochum (DE)

( * ) Notice: Subject to any disclaimer, the term of this patent is extended or adjusted under 35 U.S.C. 154(b) by 0 days.

(21) Appl. No.: 14/067,199

(22) Filed: Oct. 30, 2013

(65) Prior Publication Data
US 2014/0124682 A1    May 8, 2014

(30) Foreign Application Priority Data
Oct. 30, 2012  (DE) .......................... 10 2012 021 185

(51) Int. Cl.
*A61C 19/04*  (2006.01)
*F21V 9/14*  (2006.01)
*A61C 9/00*  (2006.01)
*G01B 11/25*  (2006.01)

(52) U.S. Cl.
CPC ................ *A61C 19/04* (2013.01); *A61C 9/006* (2013.01); *A61C 9/0053* (2013.01); *G01B 11/25* (2013.01)

(58) Field of Classification Search
CPC ..... A61C 19/04; F21V 9/14; F21W 2131/202
USPC ........................... 250/459.1, 458.1
See application file for complete search history.

(56) References Cited

U.S. PATENT DOCUMENTS

| | | | |
|---|---|---|---|
| 4,175,862 A | 11/1979 | DiMatteo et al. | |
| 4,349,277 A | 9/1982 | Mundy et al. | |
| 4,479,499 A | 10/1984 | Alfano | |
| 4,575,805 A | 3/1986 | Moermann et al. | |
| 4,648,717 A | 3/1987 | Ross et al. | |
| 4,884,860 A * | 12/1989 | Brown ........................... | 385/27 |
| 7,103,212 B2 | 9/2006 | Hager et al. | |
| 7,679,723 B2 | 3/2010 | Schwotzer | |
| 7,787,132 B2 | 8/2010 | Korner et al. | |

(Continued)

FOREIGN PATENT DOCUMENTS

| | | |
|---|---|---|
| DE | 2936847 A1 | 3/1981 |
| DE | 3003435 A1 | 8/1981 |

(Continued)

OTHER PUBLICATIONS

J.J. Ten Bosch et al., 'Optical Properties of Dentin', previously published in Dentine and Dentine Reactions in the Oral Cavity, A. Thylstrup, S.A. Leach and V. Qvist, eds. (IRL Press Ltd, Oxford, England, 1987) pp. 59-65, by permission of Oxford University Press.

(Continued)

*Primary Examiner* — Constantine Hannaher
*Assistant Examiner* — Faye Boosalis
(74) *Attorney, Agent, or Firm* — Edell, Shapiro & Finnan LLC

(57) ABSTRACT

A 3D measurement of teeth occurs while exciting fluorescence in the volume of the teeth. To this end, use is made of suitable radiation which, as a result of the fluorescence, is therefore strongly absorbed. As a result of this, the problem of translucence when measuring teeth is significantly reduced.

17 Claims, 3 Drawing Sheets

(56) References Cited

U.S. PATENT DOCUMENTS

| | | | |
|---|---|---|---|
| 8,570,530 B2 * | 10/2013 | Liang | ............................ 356/601 |
| 2004/0236232 A1 | 11/2004 | Jonusauskas et al. | |
| 2007/0248931 A1 | 10/2007 | Wong et al. | |
| 2012/0062716 A1 | 3/2012 | Dillon et al. | |

FOREIGN PATENT DOCUMENTS

| DE | 3919893 A1 | 12/1989 |
|---|---|---|
| DE | 3933994 A1 | 5/1991 |
| DE | 4027328 A1 | 3/1992 |
| DE | 4034007 A1 | 4/1992 |
| DE | 102007060263 A1 | 2/2009 |
| DE | 102007058590 A1 | 6/2009 |

OTHER PUBLICATIONS

S. Albin et al., 'Laser Induced Fluorescence of Dental Caries', Proc. SPIE 0907, Laser Surgery: Characterization and Therapeutics, p. 96-99, Jun. 15, 1988.

Frederico Frigerio, 3-Dimensional Surface Imaging Using Active Wavefront Sampling, Thesis (Ph. D.), Massachusetts Institute of Technology, Dept. of Mechanical Engineering, 2006; Abstract only—complete document is available at http://hdl.handle.net/1721.1/38258.

* cited by examiner

US 9,204,952 B2

METHOD FOR OPTICAL 3D MEASUREMENT OF TEETH WITH REDUCED POINT SPREAD FUNCTION

FIELD OF THE INVENTION

In general, the invention relates to a technique for detecting the surface shape of teeth using methods of optical 3D measurement technology. This serves for three-dimensional (3D) measurement of teeth in the mouth. This method is also referred to as taking a "digital impression".

BACKGROUND

Various optical measurement methods based on active or passive triangulation are used for teeth: phase-measuring triangulation of a strip pattern, as is described in e.g. US patent documents: M. B. Werner H. Moermann, "Method and apparatus for the fabrication of custom-shaped implants", U.S. Pat. No. 4,575,805, 1984 and G.E. Company, "Non-contact measurement of surface profile", U.S. Pat. No. 4,349,277, 1980. Other types of strip projections are described in: S.D.G. Systems "3D-Kamera zur Erfassung von Oberflächenstrukturen [3D camera for detecting surface structures]", DE 4027328, 1990;

K.& V. GmbH, "Optische Sonde zur absolutes 3-dimensionalen Vermessung von Einzelzähnen und Zahngruppen in der Mundhöhle [Optical probe for absolute 3-dimensional measurement of individual teeth and teeth groups in the oral cavity]", DE 3933994, 1989;

I. G. f. Sondermaschinenbau, "Verfahren und Vorrichtung zur berührungslosen Messung von Gestaltsabweichungen an Oberflächen [Method and device for contactless measurement of figure deviations on surfaces]", DE 3919893, 1989;

P. D. 6. R. D. Heitlinger and F. 6. W. D. Rödder "Verfahren zur Herstellung von Zahnersatz und Vorrichtung zur Durchführung des Verfahrens [Method for producing tooth replacement and device for carrying out the method]", DE 2936847, 1979;

A. D. Becker Dental-Labor GmbH, "Verfahren und Vorrichtung zur Herstellung eines Kronenteiles [Method and device for producing a crown part]". DE 3003435, 1980; and "Method of three-dimensional measurement with few projected patterns", U.S. Pat. No. 4,648,717, 1985.

Passive stereo methods are described in N. D. Steinbichler Optotechnik GmbH, "Vorrichtung zur Ermittlung der 3D-Koordinaten eines Objkts, insbesondere eines Zahns [Device for establishing the 3-D coordinates of an object, in particular of a tooth]", DE 102007060263, 2007.

Active stereo methods, active and passive multi-baseline-stereo methods are described in: B. M. Gregory, D. Hager and E. L. Wegbreit, "Acquisition of three-dimensional images by an active stereo technique using locally unique patterns", U.S. Pat. No. 7,103,212, 2003 and M. N. Solid Photography Inc, "Arrangement for sensing the geometric characteristics of an object", U.S. Pat. No. 4,175,862, 1975.

A passive multi-baseline-stereo as a result of a rotating aperture stop is described in F. Frigerio "3-dimensional surface imaging using active wavefront scanning" US 1995/2006.

Active or passive methods for triangulation are distinguished according to whether a pattern to be evaluated, irrespective of type, is projected onto the measurement object (active method) or not (passive method). The name "triangulation" is based on the fact that the camera, the projector and the point of reflection on the measurement object form a triangle.

Use is likewise made of the confocal measurement method. Unlike the aforementioned methods, this is based on the analysis of the local image sharpness or the local contrast of a light point projected onto the measurement object by means of an optical system with a large aperture, as described in "Method and arrangement for a rapid and robust chromatic confocal 3D measurement technique", U.S. Pat. No. 7,787,132-B2, 2007 and S. D. S. GmbH, "Measuring device and method that operates according to the basic principles of confocal microscopy", U.S. Pat. No. 7,679,723-B2, 2005.

The aforementioned optical measurement methods generally comprise an illumination system, which conveys light onto the teeth, and an observation system, which analyzes the light after the interaction thereof with the tooth, with the aid of a computer and evaluation unit.

In contrast to most technical measurement objects, human teeth have a pronounced translucence.

The German patent "Verfahren and Vorrichtung zur optischen Erfassung von Oberflächenstrukturen an Zähnen [Method and device for optically detecting surface structures on teeth]", DE 40 34 007 C2, 1990, discloses the practice of coating the teeth with a fluorescent dye, in particular fluorescein, in order to avoid the problem of translucence. (A)

Coating the teeth with a scattering material, e.g. titanium dioxide powder, constitutes another conventional method for avoiding translucence, as described in the aforementioned document in column 1, line 37. (B)

DE 102007058590-B4 discloses the practice of illuminating the teeth using a thin light line which is then widened to a strip pattern-like structure as a result of the translucence and using this to carry out the measurement method of strip projection. (C)

A disadvantage of the solutions (A) and (B) is the necessity of preparing the teeth. This step, firstly, is a further work step, which is connected to effort. Secondly, very sensitive areas are coated. The coating means has to be removed again because it would interfere with the adhesive connection between tooth and tooth replacement. The nerve in the tooth cannot be cleansed of the coating means without adversely affecting the nerve. On the other hand, the nerve cannot be excluded from the preparation since the whole geometry has to be detected.

SUMMARY

It is the object of the present invention to lift or at least reduce the above-described restrictions, particularly in respect of translucence.

The object is achieved by method for optically measuring teeth, comprising the following steps: emitting light in the range of at least one excitation wavelength for fluorescence, the excitation wavelengths being selected in such a way that they excite tissue and/or substances in the interior of human teeth to fluoresce such that, in the interior thereof, the teeth absorb light in the range of the excitation wavelengths as a result of fluorescence and emit light in the range of at least one emission wavelength, and detecting light in the range of the emission wavelengths or in the range of the at least one emission wavelength for signal evaluation purposes. Furthermore, the object is achieved by a device for measuring teeth, comprising an illumination unit, which is configured to emit light in the range of at least one excitation wavelength for fluorescence, the excitation wavelengths being selected in such a way that they excite tissue and/or substances in the interior of human teeth to fluoresce such that, in the interior thereof, the teeth absorb light in the range of the excitation wavelengths as a result of fluorescence and emit light in the range of at least one emission wavelength, and an observation unit, which is configured to detect light in the range of the emission wavelengths or in the range of the at least one emission wavelength, for signal evaluation purposes.

The at least one emission wavelength is preferably one or more of the following groups: 350 nm, 400 nm, 450 nm and 520 nm. As will be explained more closely in the following text in more detail, these are fluorescence wavelengths.

In a preferred embodiment of the invention, the range of the at least one emission wavelength, in which light is detected or observed, is approximately ±30 nm and preferably ±20 nm around the at least one emission wavelength. However, the invention also comprises ranges of approximately ±40 nm, ±39 nm, ±38 nm, ±37 nm, ±36 nm, ±35 nm, ±34 nm, ±33 nm, ±32 nm, ±31 nm, ±30 nm, ±29 nm, ±28 nm, ±27 nm, ±26 nm, ±25 nm, ±24 nm, ±23 nm, ±22 nm, ±21 nm, ±20 nm, ±19 nm, ±18 nm, ±17 nm, ±16 nm, ±15 nm, ±14 nm, ±13 nm, ±12 nm, ±11 nm, ±10 nm, ±9 nm, ±8 nm, ±7 nm, ±6 nm, ±5 nm, ±4 nm, ±3 nm, ±2 nm or ±1 nm around one or more of the emission wavelengths, with it also being possible for ranges with different sizes to be provided for different emission wavelengths. By way of example, it is therefore possible to simultaneously detect or observe light in the ranges from 450 nm±31 nm and 520 nm±19 nm, etc.

Advantageously, the illumination takes place in the spectral range of 370 to 420 nm and preferably in the spectral ranges of 370 to 390 nm and/or 400 to 420 nm.

Furthermore, it is preferable for the range of at least one excitation wave for fluorescence, in which light is emitted, and the range of the at least one emission wavelength, in which light is detected, to be disjointed. The excitation wavelength range is therefore different from or non-overlapping with the observed emission wavelength range, which is particularly advantageous for the utilization according to the invention of fluorescence because, in this case, there is a frequency shift between excitation and emission. As a result of this, the quality of the signal evaluation is also improved since photons which were not emitted by the fluorescence are excluded from observation or detection.

Advantageously, a filter characteristic of an optical filter in the beam path upstream of the light detection transmits at the at least one emission wavelength. Hence, provision is made in front of the observation unit for a filter with a transmission characteristic which passes the range of the at least one emission wavelength, in which light is detected, with other frequency ranges being cutoff. By way of example, the filter or filters has or have a transmission only in the ranges 450 nm±31 nm and 520 nm±19 nm.

The teeth are advantageously not prepared so that excitation light can penetrate into the tooth.

The present invention is based on the application of fluorescence, with radiated light exciting the deep tooth substance, i.e. tooth substance in the interior or in the volume of the tooth, to emit fluorescence radiation, which then, in turn, can be evaluated by an observation unit. The illumination unit and the observation unit are preferably provided as a hand-held instrument.

Here, the exciting radiation can be selected in such a way that it lies in a particularly suitable spectral range, for example from 370 nm to 420 nm.

The optical measurement by means of the observed florescence radiation can then take place using a suitable method, e.g. according to the stereo method or multi-baseline-stereo method. In the process, the observation unit can project a fine marking pattern.

By means of the present invention, it is possible to avoid complicated preparation of the teeth, with a reliable geometric detection nevertheless taking place.

Further advantageous embodiments can be gathered from the dependent claims and the further description.

BRIEF DESCRIPTION OF THE DRAWINGS

The invention will be described in more detail with reference to the attached drawings. In the figures.

DETAILED DESCRIPTION

Figure 1:
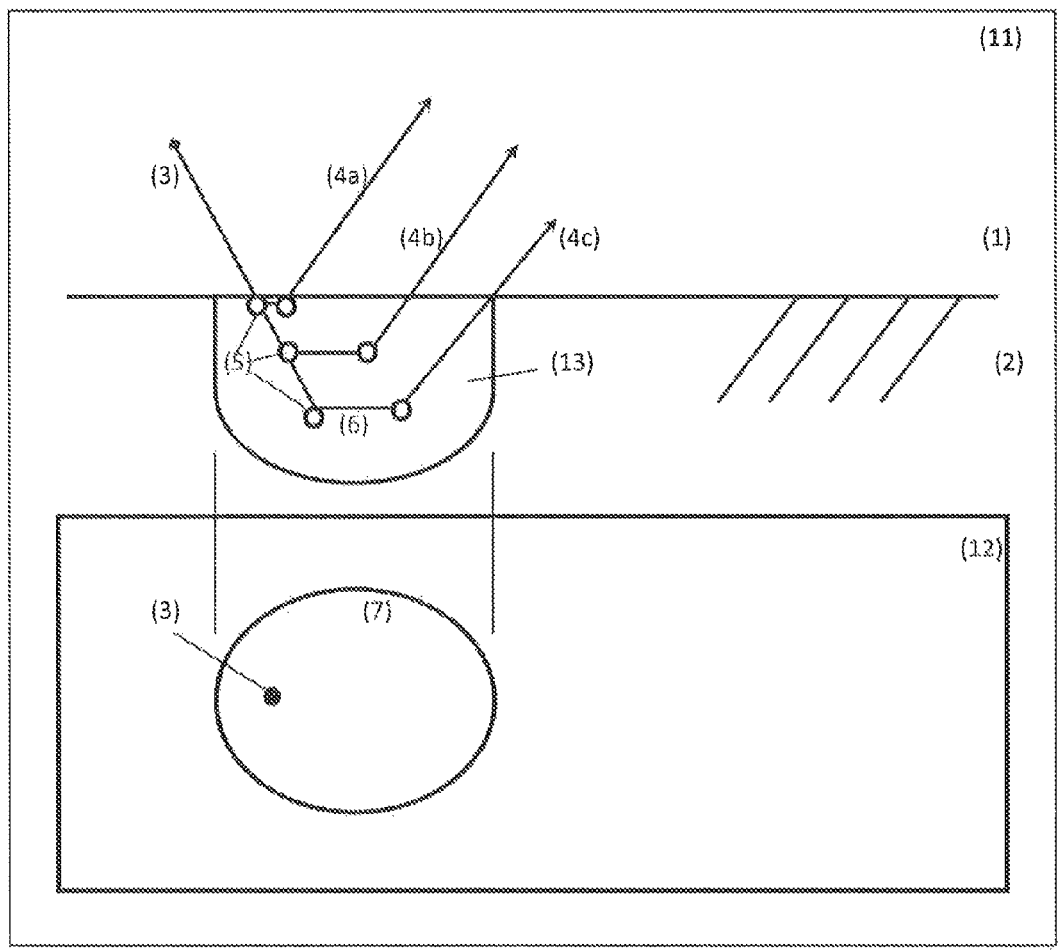
FIG. 1 shows a sectional view (11) and a top view (12) for depicting the light propagation in a translucent tissue.

The propagation of light in the translucent tissue is depicted in FIG. 1; to be precise, firstly, in a sectional image 11 on the interface between air 1 and tooth material 2 and, secondly, in a top view 12.

A light beam 3 with a wavelength $\lambda 0$ is cast onto the teeth by an illumination unit. A majority of the light of this beam penetrates deep into the tooth and is scattered once or repeatedly on scattering centers 5 below the tooth surface until it reemerges as scattered light 4 and enters the entry pupil of the observation system. The literature, e.g. "Optische Eigenschaften des Zahnbeins [Optical properties of dentin]". J. J. ten Bosch and J. R. Zijp in "Zahnbein and Zahnbeinreaktionen in der Mundhöhle [Dentin and dentin reactions in the oral cavity]", A. Thylstrup, S. A. Leach and V. Qvist, eds. (IRL Press Ltd, Oxford, England, 1987), pages 59-65, discloses values for the scattering coefficient; it is specified with values between 3 $mm^{-1}$ to $8^{-1}$ mm. Hence, these scattering centers 5 are only present with low density, and so the range R0 of multiply scattered light beams 6 in the interior or in the volume of the tooth is relatively large. From the specified scattering coefficients, it is possible to derive approximately the order of 1 mm for R0. Accordingly, the point response (point-spread function, PSF) of a point projected onto the tooth is an extended point spread 7 with moreover reduced contrast.

The signal is generated in a large signal-generation volume 13; instead of a reflection at one point, as postulated by the "triangulation" measurement principle, the whole volume is involved with the backscattering; the calculation back to the location of the scattering is correspondingly unsharp, i.e. the measurement is imprecise.

According to the invention, the "deep fluorescence" in the interior of the tooth or the fluorescence of the volume of the tooth is utilized to improve the mechanism of the signal generation. The signal-generation volume 13 is excited to fluoresce in the depth; as will be shown below, this reduces the point-spread function.

The tissue of natural teeth exhibits fluorescence in the following spectral ranges:

| Maximum excitation | Emission | Chromophore |
|---|---|---|
| 300 nm | 350 | Traces of tryptophan |
| 325 nm | 400 | Hydroxypyridinium |
| 380 nm | 450 | Unknown |
| 410 nm | 520 | Unknown |

These properties apply both to dentin (Latin: dentin) and enamel (Latin: enamelium). This data can be gathered from the document cited above.

According to the invention, the wavelength λ1 of the light, which penetrates into the tissue of the tooth, is selected in such a way that the tooth is excited to fluoresce at this wavelength λ1.

The energy of the corresponding photon P1 is: E1=h*c/λ1 (c: speed of light, h: Planck constant).

Thus, according to the invention, the photon should find molecular surroundings in the tooth volume having an energy level structure suitable for letting a fluorescence process occur.

According to the invention, it was recognized that this is advantageous since the photon is absorbed in this process and hence the tooth tissue has increased absorption at this wavelength.

According to the invention, this is utilized to avoid or reduce the translucence of the teeth. In the translucence mechanism, light, as already mentioned above, penetrates the tooth, passes over a path of length R0 therein, leaves the tooth again and enters the entry pupil of the observation system.

Figure 2:
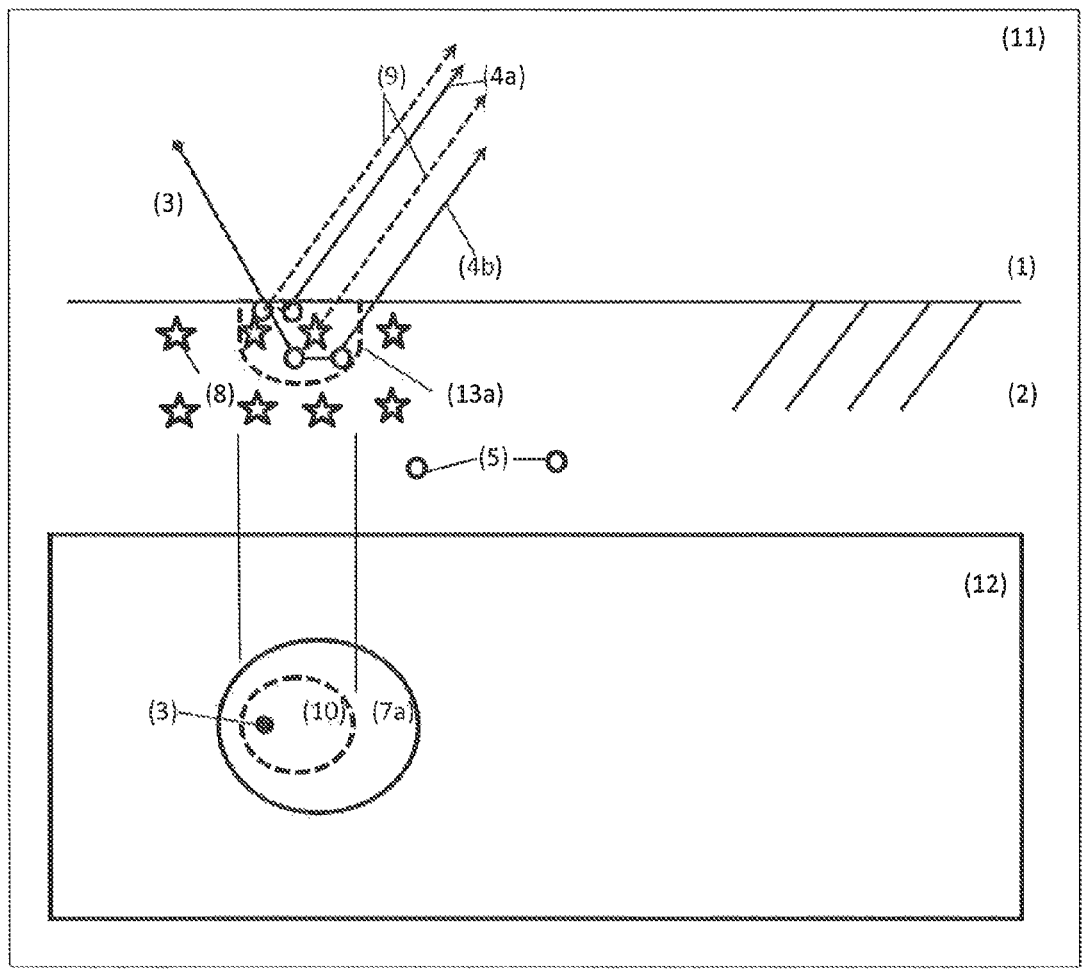
FIG. 2 shows the increased absorption by fluorescence which, according to the invention, is utilized to reduce the translucence.

This is explained in FIG. 2: the presence of fluorescence-capable molecules in the volume 8 leads to the presence of absorption which reduces the range of the light in the tooth since it is absorbed along its path. Long light paths become rarer; short light paths are less affected by the absorption. Thus, the light of wavelength λ1 will on average only pass over a path length R1 which is less than R0; the point spread 7a becomes smaller than the point spread 7 at the wavelength λ0, without the presence of fluorescence in the volume.

With the point spread 7a at the wavelength λ1 there is simultaneously a second point spread 10 at the fluorescence wavelength λ2.

The point spread 10 for the light beams of the wavelength λ2 9 is less than the point spread 7a at the wavelength λ1. The reason for this is that the photons emitted in the fluorescence process in the volume had already experienced a random change in direction and are potentially able to reach the pupil of the observation directly, i.e. without further scattering. Photons of the wavelength λ1, which were not absorbed, require a further scattering process, increasing the point spread. Thus, there is an improvement in the point spread at both wavelengths, but it is more pronounced at the wavelength λ2.

According to the invention, the observation takes place at the wavelength λ2. The deep fluorescence in the interior of the tooth, i.e. the fluorescence of the volume or of the volume through which light passes, thus leads to the signal generation volume 13a for light of the wavelength λ2 being less than, in the case without fluorescence, the signal generation volume 13 for light of the wavelength λ0; it is accordingly possible to more precisely calculate back to the location of scattering, i.e. the measurement is more precise than the measurement without the involvement of fluorescence in the tissue.

In all images, full lines are used for light beams of the wavelength λ1 and dashed lines are used for light beams of the wavelength λ2.

Compared to the prior art, the invention has the advantage of reducing the point spread without preparing the tooth.

In some embodiments, several fluorescence wavelengths present in the volume are combined. Thus, the filter characteristic of an optical filter in the beam path of the illumination and observation apparatus must in each case only be expanded by the transmission in one further spectral range in order to be able to utilize simultaneously two fluorescence effects present in the volume. As a result, the light yields of both fluorescence effects are combined, without further components having to be added to the system.

In one embodiment, use is made, in particular, of the maxima at 380 and 410 nm, or the combination of both, since these are of particular interest for technical use in an intraoral 3D measurement as a result of it being possible to use conventional optical materials.

It is not necessary to generate the illumination wavelength λ1 with monochromatic light. The phenomenon of fluorescence in principle occurs in a characteristic spectral range, the characteristic wavelength of which merely represents an optimum. For reasons of light yield, a spectral range about the maximum is always used in the technical realization. For practical applications, a spectral range of approximately +/−10 nm is necessary in order to ensure sufficient luminous intensity.

For the maximum at 380 nm, the illumination can therefore occur in the spectral range 370-390 nm. For the maximum at 410 nm, the illumination can occur around the spectral range of 400 nm to 420 nm.

Figure 3:
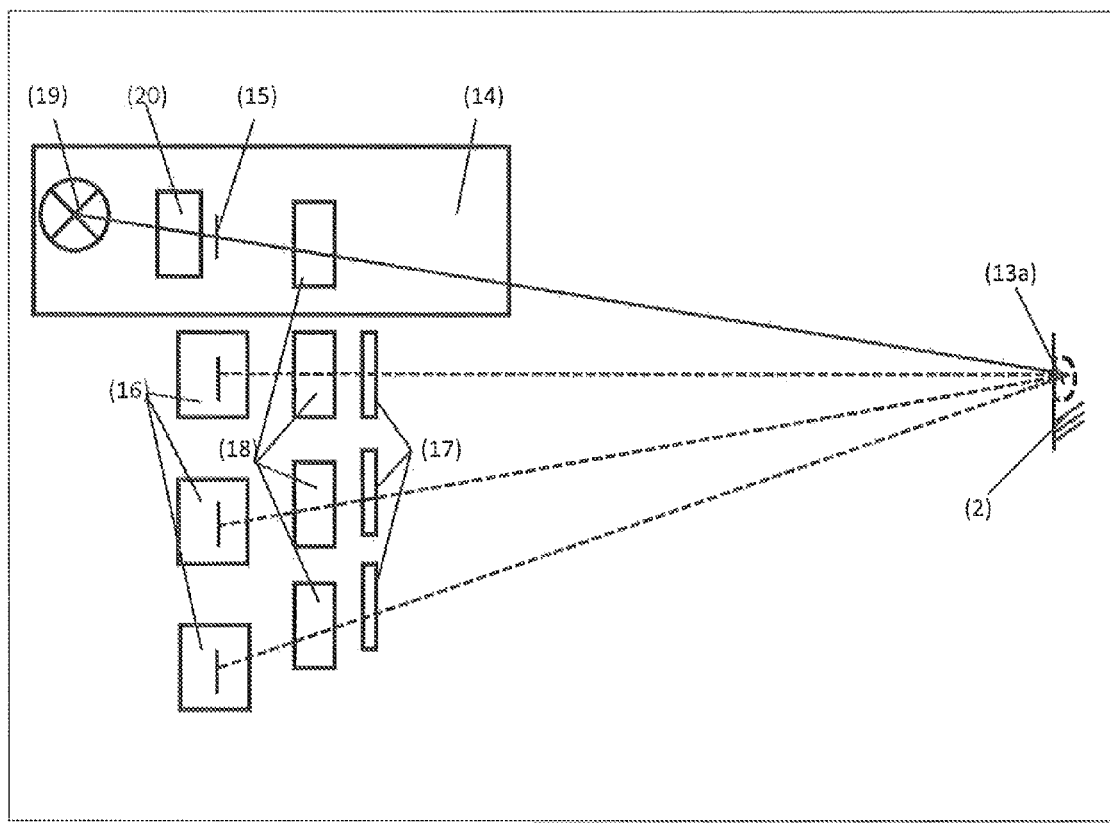
FIG. 3 shows a device for implementing the concept of deep fluorescence or fluorescence in the volume, with an active stereo method and a multi-baseline-stereo method being configured in this embodiment and a fine marking pattern being projected.

In one embodiment of the device of FIG. 3 of the invention, this is utilized to realize a measurement method known in dentistry, in which a small PSF is of particular importance: the known active stereo method and multi-baseline-stereo method requires a fine marking pattern, which needs to have a higher resolution than the subsequent 3D structure resolution of the 3D measurement system. In practical cases, an approximately 3-fold higher resolution is required. With the technology of utilizing the "deep fluorescence or the fluorescence of the volume (through which light passes)", it is possible to obtain such a pattern with high-resolution when it interacts with the tooth tissue 2.

Compared thereto, the scanner described in the German patent application DE 102007060263 has a lower resolution (provided work is not undertaken with preparations) because the described technique is not utilized.

In the device according to the invention, it is possible for the illumination to be able to take place with an LED 19 having a condenser 20, which emits in the range 370 nm-420 nm. This results in an illumination unit, in which a filter at the projector 14 can be dispensed with on the illumination side 14. The projector projects a mask 15 with a marking pattern onto the tooth. If the mean spectral range 390-400 nm does not have fluorescence in the tissue either, or if it only has little fluorescence, it is harmless because it is filtered out on the observation side.

The observation unit comprises at least two video cameras 16 with lenses 18, but in each case with an optical filter 17, which excludes wavelengths below 420 nm from the observation.

"Optische Eigenschaften Zahnbein [Optical properties of dentin]". J. J. ten Bosch and J. R. Zijp in "Zahnbein and Zahnbeinreaktionen in der Mundhöhle [Dentin and dentin reactions in the oral cavity]", A. Thylstrup, S. A. Leach and V. Qvist, eds. (IRL Press Ltd, Oxford, England, 1987), pages 59-65 denotes the chemical reason for fluorescence of the tissue as unknown. Possibly, this is not an effect of natural teeth, but rather an effect of constituents of toothpaste that penetrated into the tissue and have remained there long-term. Thus, the term "fluorescence in the tissue of teeth or deep in the tooth or in the volume of the tooth" should be understood to mean the fluorescence in the tissue of real human teeth at the current time, including environmental effects.

The signal evaluation of the signals recorded by the observation unit can take place in a manner known per se.

LIST OF REFERENCE SIGNS USED IN THE FIGURES (PART OF THE DESCRIPTION)

1: Air
2: Tooth material
3: Light beam from the illumination system
4a 4b 4c: Scattered light beams which reach the entry pupil of the observation
5: Low density scattering centers
6: Multiply scattered light beam
7: Point spread of (3)
7a: Point spread of (3), when fluorescence is lacking, at the excitation wavelength
8: Fluorescence-capable molecules in the volume
9: Light beams emitted by fluorescence, which reach the entry pupil of the observation
10: Point spread of 3 at the fluorescence wavelength
11: Sectional image
12: Top view
13: Signal-generation volume
14: Projector for fine patterns, 370 to 420 nm
15: Mask with marking pattern
16: Cameras
17: Filters
18: Lenses
19: LED (370-420 nm)
20: Condenser

The invention claimed is:

1. A method for optically measuring teeth, comprising:
emitting light in the range of at least one excitation wavelength for fluorescence, the excitation wavelengths being selected such that they excite tissue and/or substances in the interior of human teeth to fluoresce such that, in the interior thereof, the teeth absorb light in the range of the excitation wavelengths as a result of fluorescence and emit light in the range of at least one emission wavelength,
detecting light as emitted fluorescence radiation in the range of the at least one emission wavelength for signal evaluation, wherein at least a portion of the detected light is outside the range of excitation wavelengths, and
optically measuring a three-dimensional surface shape of the teeth using the emitted fluorescence radiation.

2. The method according to claim 1, wherein the at least one emission wavelength is one or more of the following groups: 350 nm, 400 nm, 450 nm and 520 nm.

3. The method according to claim 1, wherein the range of the at least one emission wavelength, in which light is detected, is ±30 nm around the at least one emission wavelength.

4. The method according to claim 3, wherein the range of the at least one emission wavelength, in which light is detected, is ±20 nm around the at least one emission wavelength.

5. The method according to claim 1, wherein the illumination takes place in the spectral range of 370 to 420 nm.

6. The method according to claim 1, wherein the range of at least one excitation wave for fluorescence, in which light is emitted, and the range of the at least one emission wavelength, in which light is detected, are disjoint.

7. The method according to claim 1, wherein an optical measurement operates according to a stereo method or a multi-baseline-stereo method, and a fine marking pattern is projected.

8. The method according to claim 1, wherein a filter characteristic of an optical filter in the beam path upstream of the light detection transmits at the at least one emission wavelength.

9. The method according to claim 1, wherein the teeth have not been prepared.

10. A device for optically measuring teeth, comprising
an illumination unit configured to emit light in the range of at least one excitation wavelength for fluorescence, the excitation wavelengths being selected such that they excite tissue and/or substances in the interior of human teeth to fluoresce such that, in the interior thereof, the teeth absorb light in the range of the excitation wavelengths as a result of fluorescence and emit light in the range of at least one emission wavelength,
an observation unit configured to detect light as emitted fluorescence radiation in the range of the at least one emission wavelength for signal evaluation, wherein at least a portion of the emitted fluorescence radiation is outside the range of excitation wavelengths, and optically measure a three-dimensional surface of the teeth using the emitted fluorescence radiation.

11. The device according to claim 10, wherein the at least one emission wavelength is one or more of the following groups: 350 nm, 400 nm, 450 nm and 520 nm.

12. The device according to claim 10, wherein the range of the at least one emission wavelength, in which light is detected, is ±30 nm around the at least one emission wavelength.

13. The device according to claim 12, wherein the range of the at least one emission wavelength, in which light is detected, is ±20 nm around the at least one emission wavelength.

14. The device according to claim 10, wherein the illumination unit emits in the spectral range of 370 to 420 nm.

15. The device according to claim 10, wherein the range of at least one excitation wave for fluorescence, in which light is emitted, and the range of the at least one emission wavelength, in which light is detected, are disjointed.

16. The device according to claim 10, wherein an optical measurement operates according to a stereo method or multi-baseline-stereo method, and in that the observation unit projects a fine marking pattern.

17. The device according to claim 10, wherein a filter characteristic of an optical filter in the beam path upstream of the light detection transmits at the at least one emission wavelength.

* * * * *